(12) United States Patent
Crucs

(10) Patent No.: US 7,876,878 B2
(45) Date of Patent: Jan. 25, 2011

(54) AUTOMATIC SPATIAL ADJUSTMENT OF A PAN-ORAL X-RAY SOURCE IN RESPONSE TO THE ACTUAL DENTITION OF A PATIENT

(75) Inventor: Kevin M. Crucs, Akron, OH (US)

(73) Assignee: Apteryx, Inc., Akron, OH (US)

( * ) Notice: Subject to any disclaimer, the term of this patent is extended or adjusted under 35 U.S.C. 154(b) by 10 days.

(21) Appl. No.: 12/342,418

(22) Filed: Dec. 23, 2008

(65) Prior Publication Data

US 2010/0159414 A1 Jun. 24, 2010

(51) Int. Cl.
*A61B 6/14* (2006.01)

(52) U.S. Cl. .............................. 378/39; 378/38; 378/40

(58) Field of Classification Search .............. 378/38–40
See application file for complete search history.

(56) References Cited

U.S. PATENT DOCUMENTS

| 3,806,732 | A | * | 4/1974 | Kataoka et al. ............... 378/40 |
| 3,932,756 | A | | 1/1976 | Cowell et al. |
| 4,044,265 | A | | 8/1977 | Schmidt |
| 4,125,774 | A | | 11/1978 | Ciavattoni et al. |
| 5,842,858 | A | | 12/1998 | Truppe |
| 7,336,763 | B2 | | 2/2008 | Spartiotis et al. |
| 7,676,022 | B2 | | 3/2010 | Pantsar et al. |
| 7,688,941 | B2 | * | 3/2010 | Thoms ........................ 378/38 |
| 2007/0207441 | A1 | | 9/2007 | Lauren |
| 2009/0274267 | A1 | * | 11/2009 | Mandelkern et al. .......... 378/39 |

FOREIGN PATENT DOCUMENTS

KR 10-2001-0014044 A 2/2001

* cited by examiner

*Primary Examiner*—Jurie Yun
(74) *Attorney, Agent, or Firm*—Hahn Loeser & Parks LLP

(57) ABSTRACT

A system, method, and computer program product for performing pan-oral imaging. A plurality of data points are generated which are representative of spatial positions of an actual dentition of a patient with respect to a defined spatial coordinate system. A fitted curve through at least a portion of the spatial positions of the dentition is computed using the plurality of data points. A pan-oral image acquisition trajectory is then computed with respect to a defined spatial coordinate system using the fitted curve. A pan-oral image of the dentition is then acquired along the pan-oral image acquisition trajectory.

32 Claims, 8 Drawing Sheets

AUTOMATIC SPATIAL ADJUSTMENT OF A PAN-ORAL X-RAY SOURCE IN RESPONSE TO THE ACTUAL DENTITION OF A PATIENT

CROSS-REFERENCE TO RELATED APPLICATIONS/INCORPORATION BY REFERENCE

U.S. Pat. No. 3,932,756, issued Jan. 13, 1976 to Cowell et al., is incorporated herein by reference in its entirety as background and support information related to pan-oral imaging. U.S. Pat. No. 4,044,265, issued Aug. 23, 1977 to Schmidt, is incorporated herein by reference in its entirety as background and support information related to pan-oral imaging. U.S. Pat. No. 4,125,774, issued Nov. 14, 1978 to Ciavattoni et al., is incorporated herein by reference in its entirety as background and support information related to pan-oral imaging.

TECHNICAL FIELD

Certain embodiments of the present invention relate to pan-oral imaging. More particularly, certain embodiments relate to a system and method for the automatic spatial adjustment of a pan-oral x-ray source in response to the actual dentition of a patient.

BACKGROUND

Panoramic radiography is a well known mode of imaging used in dentistry. Panoramic radiographs (a.k.a. pan-oral images) provide an overall view of the dentomaxillofacial complex and are used to aid patient diagnosis.

When attempting to image the dentition of a patient to form a pan-oral image, it is desirable to have the dentition be within the focal trough formed by the pan-oral imaging system (a.k.a. a panoramic imaging system). In general, a focal trough is a horseshoe-shaped zone of sharpness used by the pan-oral x-ray system and is generally fixed in three-dimensional space. Dentition placed within the focal trough will appear relatively clear and in focus on a film or display. The focal trough of the pan-oral x-ray system is a three-dimensional curved zone in which dentition and other structures are reasonably well defined on the panoramic radiographs. Structures behind or in front of the focal trough will tend to be distorted, reduced in size, blurred, or magnified. Therefore, the limited dimensions of the focal trough with respect to the patient's dentition, operator error, and machine age or misalignment may cause errors to occur in the anatomy of interest shown on the acquired image.

Today, a number of different approximation profiles of dentition may be collected and stored in a pan-oral imaging machine. A user may then select the approximation profile that the user decides is the closest match to the current patient. The pan-oral imaging machine will then follow that profile, regardless of the actual dentition of the patient.

Further limitations and disadvantages of conventional, traditional, and proposed approaches will become apparent to one of skill in the art, through comparison of such approaches with the subject matter of the present application as set forth in the remainder of the present application with reference to the drawings.

SUMMARY

An embodiment of the present invention comprises a method of performing pan-oral imaging. The method includes generating a plurality of data points representative of spatial positions of an actual dentition of a patient with respect to a defined spatial coordinate system. The method further includes computing a fitted curve through at least a portion of the spatial positions of the dentition using the plurality of data points. The fitted curve may be computed from spatial positions of an upper dentition of the patient, spatial positions of a lower dentition of the patient, or both. The computing of the fitted curve may be accomplished using a least squares technique or some other linear regression technique, for example. The method also includes computing a pan-oral image acquisition trajectory with respect to the defined spatial coordinate system using the fitted curve. The method further includes acquiring a pan oral image of the dentition along the pan-oral image acquisition trajectory.

In accordance with an embodiment of the present invention, the acquiring of the pan-oral image is accomplished, at least in part, by providing an incident direction of x-ray radiation substantially perpendicular to points along the fitted curve within the defined spatial coordinate system. Furthermore, in accordance with an embodiment of the present invention, the acquiring of the pan-oral image is accomplished, at least in part, by forming a focal trough containing the fitted curve within the defined spatial coordinate system.

Another embodiment of the present invention comprises a method of performing pan-oral imaging. The method includes providing a bite plate having a known spatial position and orientation in three-dimensional space with respect to a defined three-dimensional spatial coordinate system. The method further includes having a patient position the bite plate within a mouth of the patient and bite down on the bite plate. The method also includes the bite plate producing a plurality of electrical signals in response to the biting down, wherein the plurality of electrical signals are representative of spatial positions of a dentition of the patient with respect to the defined three-dimensional spatial coordinate system. The method further includes communicating the plurality of electrical signals to a computer-based platform. The method also includes the computer-based platform computing a fitted curve through at least a portion of the spatial positions of the dentition in response to the electrical signals. The fitted curve may be computed from spatial positions of an upper dentition of the patient, spatial positions of a lower dentition of the patient, or both. The computing of the fitted curve may be accomplished using a least squares technique or some other linear regression technique, for example. The method further includes the computer-based platform computing a pan-oral image acquisition trajectory with respect to the defined three-dimensional spatial coordinate system in response to the fitted curve. The method also includes acquiring a pan-oral image of the dentition by moving an x-ray source along the pan-oral image acquisition trajectory.

In accordance with an embodiment of the present invention, the acquiring of the pan-oral image is accomplished, at least in part, by providing an incident direction of x-ray radiation from the x-ray source substantially perpendicular to points along the fitted curve within the defined three-dimensional spatial coordinate system. Furthermore, in accordance with an embodiment of the present invention, the acquiring of the pan-oral image is accomplished, at least in part, by the x-ray source forming a focal trough containing the fitted curve within the defined three-dimensional spatial coordinate system.

A further embodiment of the present invention comprises a system for performing pan-oral imaging. The system includes means for generating a plurality of electrical signals representative of spatial positions of an actual dentition of a patient with respect to a defined spatial coordinate system. The system further includes means for computing a fitted curve through at least a portion of the spatial positions of the dentition using the plurality of electrical signals. The fitted curve may be computed from spatial positions of an upper dentition of the patient, spatial positions of a lower dentition of the patient, or both. The means for computing the fitted curve may use a least squares technique or some other linear regression technique, for example. The system also includes means for computing a pan-oral image acquisition trajectory with respect to the defined spatial coordinate system using the fitted curve. The system further includes means for acquiring a pan-oral image of the dentition along the pan-oral image acquisition trajectory.

In accordance with an embodiment of the present invention, the means for acquiring is capable of providing an incident direction of x-ray radiation substantially perpendicular to points along the fitted curve within the defined spatial coordinate system. Furthermore, in accordance with an embodiment of the present invention, the means for acquiring is capable of forming a focal trough containing the fitted curve within the defined spatial coordinate system.

Another embodiment of the present invention comprises a method of generating a pan-oral image acquisition trajectory for an x-ray imaging source. The method includes providing a pressure sensitive bite plate having a known spatial position and orientation in three-dimensional space with respect to a defined three-dimensional spatial coordinate system. The method further includes having a patient position the bite plate within a mouth of the patient and bite down on the bite plate to create points of pressure on the bite plate. The method also includes the bite plate producing a plurality of electrical signals in response to the biting down, wherein the plurality of electrical signals are representative of spatial positions of a dentition of the patient at the points of pressure with respect to the defined three-dimensional spatial coordinate system. The method further includes communicating the plurality of electrical signals to a computer-based platform. The method also includes the computer-based platform computing a fitted curve through at least a portion of the spatial positions of the dentition in response to the electrical signals. The fitted curve may be computed from spatial positions of an upper dentition of the patient, spatial positions of a lower dentition of the patient, or both. The computing of the fitted curve may be accomplished using a least squares technique or some other linear regression technique, for example. The method further includes the computer-based platform computing a pan-oral image acquisition trajectory with respect to the defined three-dimensional spatial coordinate system in response to the fitted curve.

A further embodiment of the present invention comprises a computer program product, comprising a computer usable medium having a computer readable program code embedded therein, the computer readable program code adapted to be executed to implement a method for generating a pan-oral image acquisition trajectory. The method includes reading a plurality of data points representative of spatial locations of an actual dentition of a patient with respect to a defined spatial coordinate system. The method further includes computing a fitted curve through at least a portion of the spatial positions of the dentition using the plurality of data points. The computing of the fitted curve may be accomplished using a least squares technique or some other linear regression technique, for example. The method also includes computing points of image acquisition that are projected substantially perpendicularly outward from points along the fitted curve at a defined focal distance within the defined spatial coordinate system, wherein the points of image acquisition define a pan-oral image acquisition trajectory which may be traversed by an image acquisition source. The computing of the points of image acquisition may be accomplished using a geometric projection technique.

These and other novel features of the subject matter of the present application, as well as details of illustrated embodiments thereof, will be more fully understood from the following description and drawings.

DETAILED DESCRIPTION

Figure 1:
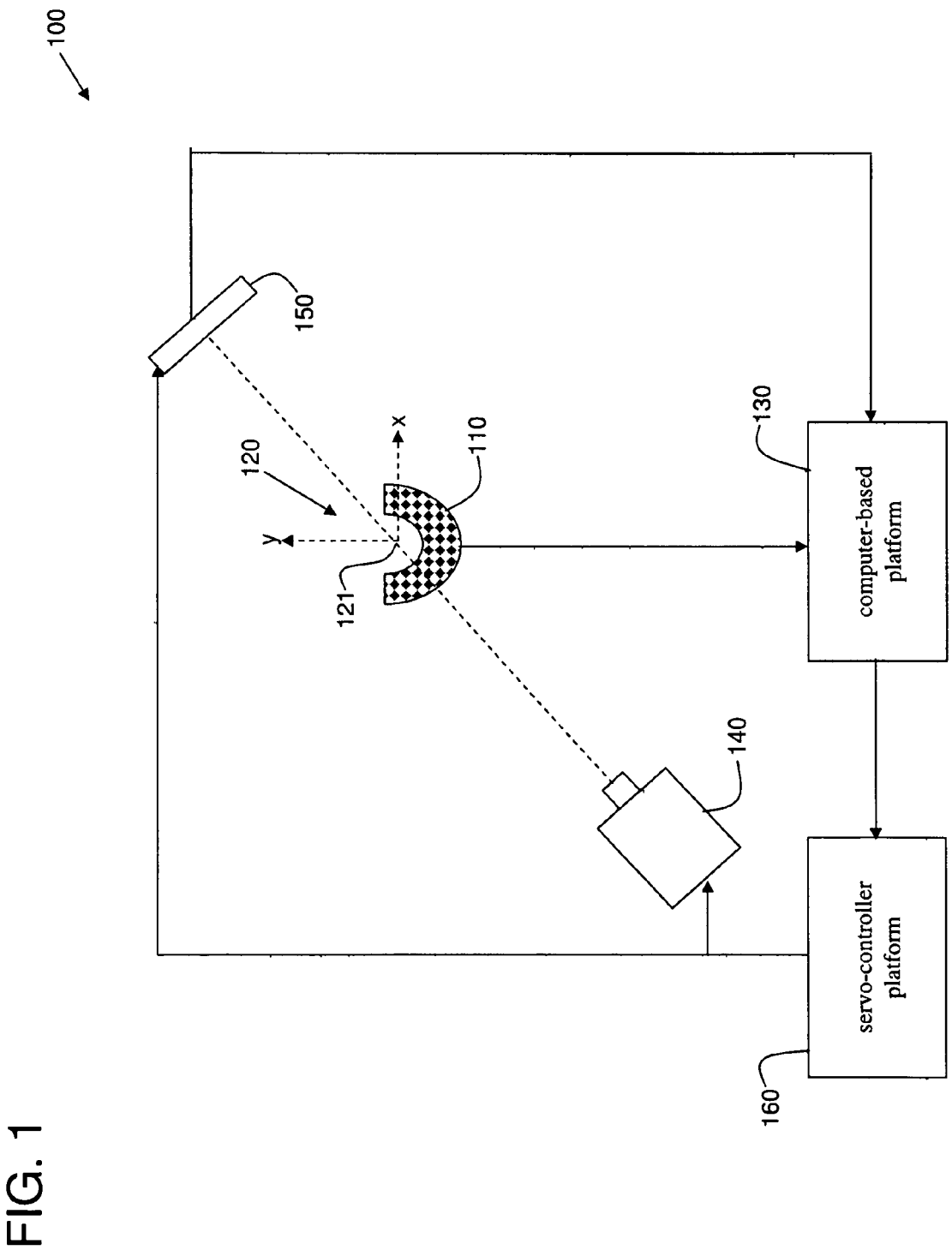
FIG. 1 illustrates a schematic block diagram of an example of an embodiment of a system for performing pan-oral imaging.

FIG. 1 illustrates a schematic block diagram of an example of an embodiment of a system 100 for performing pan-oral imaging. The system 100 includes a pressure-sensitive bite plate 110 fixedly positioned with respect to a defined spatial coordinate system 120 having an origin 121. The spatial coordinate system 120 may be a two-dimensional spatial coordinate system defined in two-dimensional space (e.g., an x-y plane) or a three-dimensional spatial coordinate system defined in three-dimensional space (x, y, z), in accordance with various embodiments of the present invention.

The bite plate 110 is constructed to fit within a patient's mouth between the teeth or dentition of the patient such that the patient is able to bite down on the bite plate 110 (using both upper and lower teeth). The bite plate 110 may be U-shaped or a solid half-oval shape, for example. The bite plate 110 includes a plurality of piezoelectric sensors distributed across an upper surface and/or a lower surface of the bite plate 110. Each piezoelectric sensor is positioned on the bite plate 110 at a known position with respect to the spatial coordinate system 120.

When a patient bites down on the bite plate 110, the piezoelectric sensors are able to sense pressure created by the teeth on the bite plate 110 and convert the sensed pressure to electrical signals. In accordance with an embodiment of the present invention, the electrical signals may be digital electrical signals representing applied pressure (e.g., a digital "1") or no applied pressure (e.g., a digital "0") on the various piezoelectric sensors. In this manner, a mapping of data points may be created within the spatial coordinate system 120 being representative of spatial positions of the actual dentition of the patient where the dentition makes contact with the bite plate 110 (i.e., forms a characteristic pattern of the actual dentition). Other types of pressure sensitive sensors (other than piezoelectric sensors) may be used, in accordance with alternative embodiments of the present invention. As a further alternative, some other type of non-pressure sensors may be used that, for example, simply indicate where the dentition makes contact with the bite plate. In accordance with an embodiment of the present invention, the bite plate 110 includes a memory device capable of storing the electrical signals generated by the piezoelectric (or other) sensors.

The system 100 also includes a computer-based platform 130 operatively connected to the bite plate 110 to receive the electrical signals generated by the bite plate 110 and to process the electrical signals in accordance with various methods described herein. Methods of communicating such electrical signals (digital information) from one device to another are well known in the art. The computer-based platform may include a software programmable personal computer (PC), a work station, an application specific processor, or a hardware programmable device, for example, capable of performing the methods described herein.

The system 100 further includes an imaging source 140 (e.g., an x-ray source) and a detector 150 (e.g., a digital x-ray detector or x-ray film cartridge) positioned directly across from the imaging source 140. The bite plate 110 is positioned between the imaging source 140 and the detector 150 such that radiative energy (e.g., x-rays) emitted by the imaging source 140 project through the patient at the bite plate 110 and are captured by the detector 150. Such imaging sources and detectors are well known in the art. The detector is operatively connected to the computer-based platform 130 to receive imaging data from the detector 150, in accordance with an embodiment of the present invention. In accordance with an alternative embodiment of the present invention, a separate image processing platform is provided which receives imaging data from the detector 150. The current spatial relationship between the bite plate 110 and the imaging source 140 is known. A sterilizing sleeve may be placed over the bite plate 110 during use.

The system also includes a servo-controller platform 160 operatively connected to the computer-based platform 130, the imaging source 140 and the detector 150. The imaging source 140 and the detector 150 may be referred to in combination herein as the imaging subsystem. The servo-controller platform 160 is capable of moving the imaging source 140 to determined locations within the defined spatial coordinate system 120 as commanded by the computer-based platform 130, and keeping the detector 150 properly positioned across from the imaging source 140 as the imaging source 140 moves.

In accordance with one embodiment of the present invention, instead of simply rotating the imaging subsystem about a single vertical axis, the servo-controller platform 160 is capable of moving the imaging subsystem in three-dimensional space having up to six degrees of freedom (6DoF) including forward/backward, up/down, left/right (translation in three perpendicular axes) combined with rotation about three perpendicular axes (yaw, pitch, roll). Other numbers of degrees of freedom are possible as well, in accordance with various alternative embodiments of the present invention. For example, the x-ray source 140 may be continuously adjusted in (x, y, z) space by the servo-controller platform 160 as the x-ray source 140 is rotated around a patient's head. Such servo-controller platforms are well known.

Figure 2:
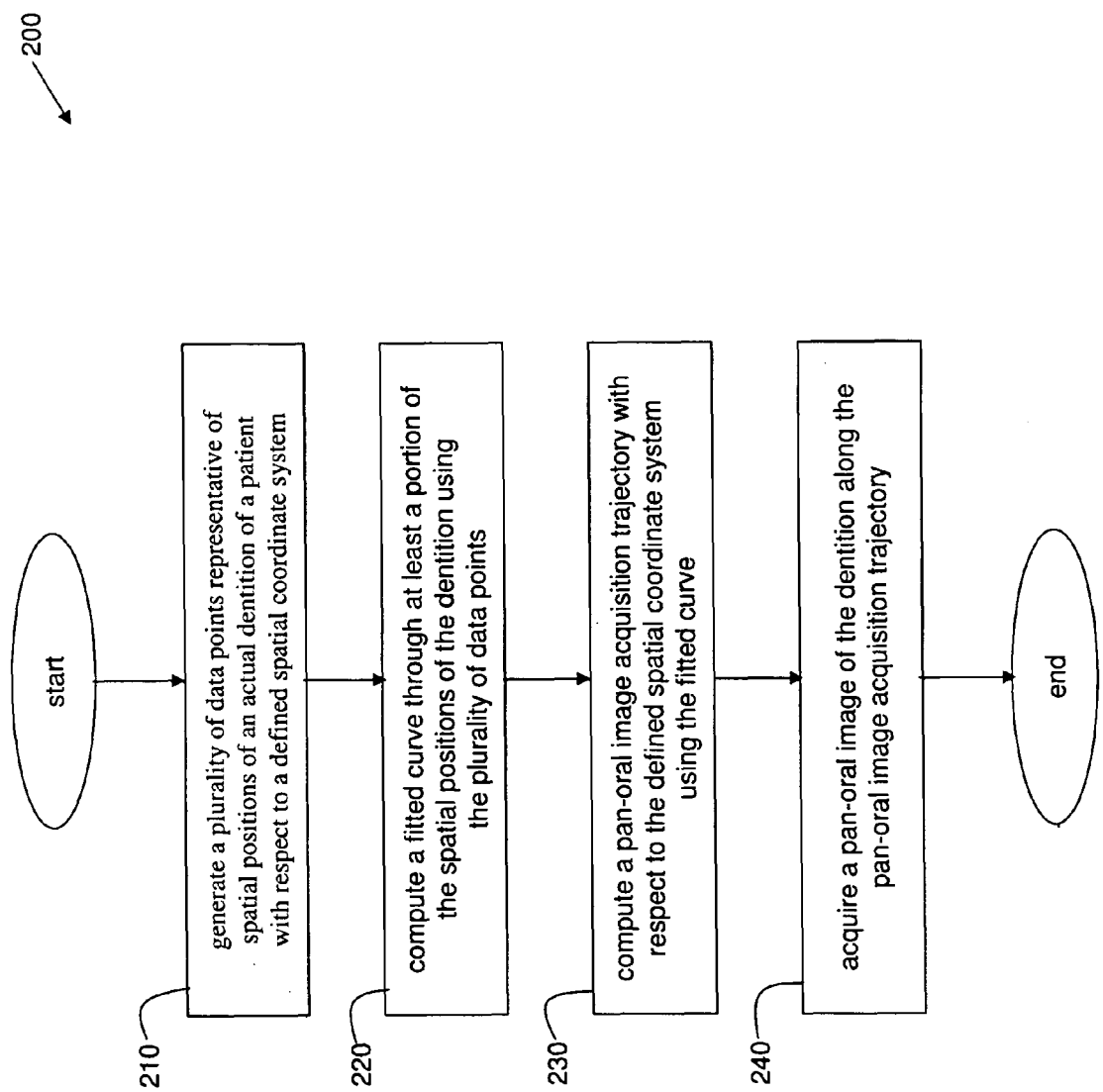
FIG. 2 is a flow chart of a first embodiment of a method for performing pan-oral imaging.

FIG. 2 is a flow chart of a first embodiment of a method 200 for performing pan-oral imaging. In step 210 of the method 200, generate a plurality of data points representative of spatial positions of an actual dentition of a patient with respect to a defined spatial coordinate system. In accordance with an embodiment of the present invention, the plurality of data points are derived from the pressure-sensitive bite plate 110 in real time. In step 220, compute a fitted curve through at least a portion of the spatial positions of the dentition using the plurality of data points.

The fitted curve may be computed from spatial positions of an upper dentition of the patient, spatial positions of a lower dentition of the patient, or both. Alternatively, multiple fitted curves may be computed. For example, a first fitted curve may be computed for the upper dentition and a second fitted curve may be computed for the lower dentition. Multiple fitted curves corresponding to other portions of dentition are possible as well. In this manner, the system 100 may create multiple images by scanning along the various fitted curves, or create a single pan-oral image by transitioning from one fitted curve to another, for example. Furthermore, the fitted curve may be updated in real time during an image acquisition scanning session as the patient may move his/her bite on the bite plate 110. Alternatively, just an initial set of bite plate data may be used to accomplish the scan.

The computing of a fitted curve may be accomplished using a least squares technique or some other linear regression technique, for example, resulting in a best-fit curve. In step 230, compute a pan-oral image acquisition trajectory with respect to the defined spatial coordinate system using the fitted curve. The pan-oral image acquisition trajectory is the spatial trajectory that will be traversed by the imaging source 140. In step 240, acquire a pan-oral image of the dentition of the patient along the pan-oral image acquisition trajectory. In accordance with an embodiment of the present invention, steps 201-240 are performed while the patient is biting down on the pressure-sensitive bite plate 110.

The pan-oral image may be acquired such that an incident direction of x-ray radiation from an x-ray source is substantially perpendicular to points along the fitted curve within the defined spatial coordinate system. Furthermore, the pan-oral image may be acquired such that a focal trough is formed by an x-ray source, where the focal trough contains the fitted curve within the defined spatial coordinate system.

Figure 3:
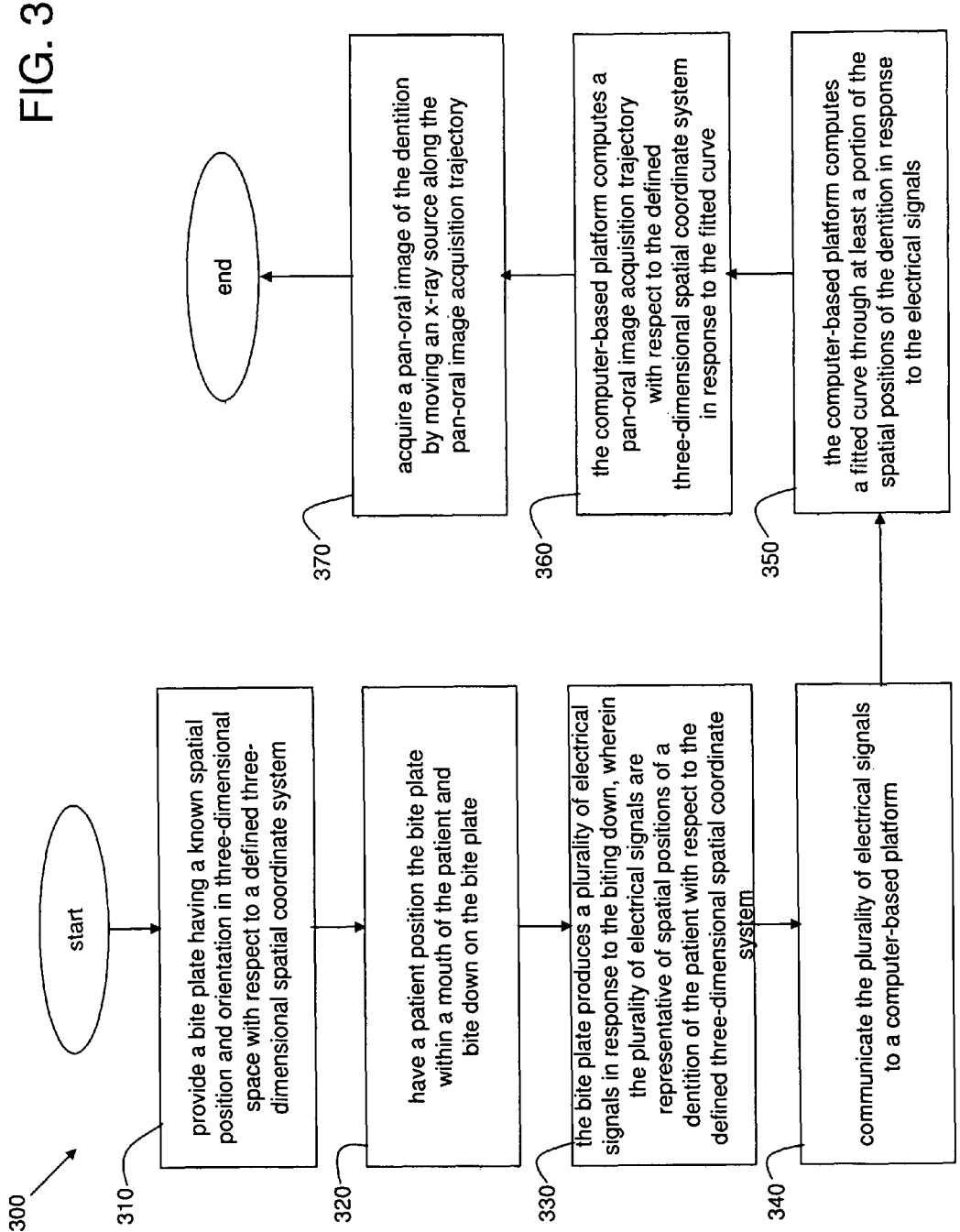
FIG. 3 is a flow chart of a second embodiment of a method for performing pan-oral imaging.

FIG. 3 is a flow chart of a second embodiment of a method 300 for performing pan-oral imaging. In step 310 of the method 300, provide a bite plate having a known spatial position and orientation in three-dimensional space with respect to a defined three-dimensional spatial coordinate system. The bite plate 110 is secured with respect to the defined spatial coordinate system. In step 320, have a patient position the bite plate within a mouth of the patient and bite down on the bite plate. A chin rest may be provided for the patient to rest his/her chin while biting down on the bite plate.

In step 330, the bite plate produces a plurality of electrical signals in response to the biting down, wherein the plurality of electrical signals are representative of spatial positions of a dentition of the patient with respect to the defined three-dimensional spatial coordinate system. In step 340, communicate the plurality of electrical signals to a computer-based platform. In step 350, the computer-based platform computes a fitted curve through at least a portion of the spatial positions of the dentition in response to the electrical signals.

Again, the fitted curve may be computed from spatial positions of an upper dentition of the patient, spatial positions of a lower dentition of the patient, or both. The computing of the fitted curve may be accomplished using a least squares technique or some other linear regression technique, for example, resulting in a best-fit curve. In step 360, the computer-based platform computes a pan-oral image acquisition trajectory with respect to the defined three-dimensional spatial coordinate system in response to the fitted curve.

In step 370, acquire a pan-oral image of the dentition by moving an x-ray source along the pan-oral image acquisition trajectory. The pan-oral image may be acquired such that an incident direction of x-ray radiation from an x-ray source 140 is substantially perpendicular to points along the fitted curve within the defined spatial coordinate system. Furthermore, the pan-oral image may be acquired such that a focal trough is formed by an x-ray source 140, where the focal trough contains the fitted curve within the defined spatial coordinate system.

Figure 4:
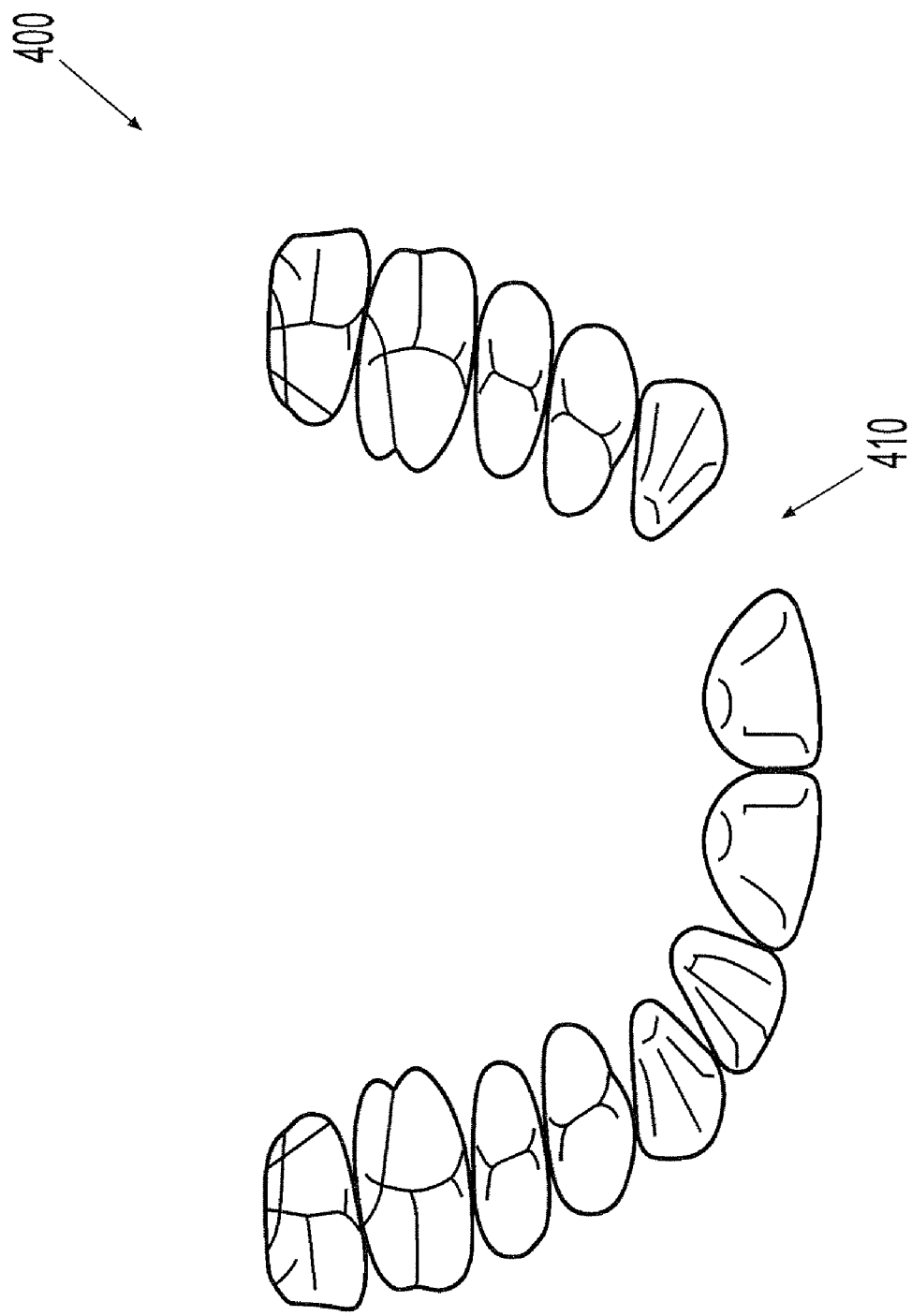
FIG. 4 illustrates an example of a dentition of a patient.
Figure 5:
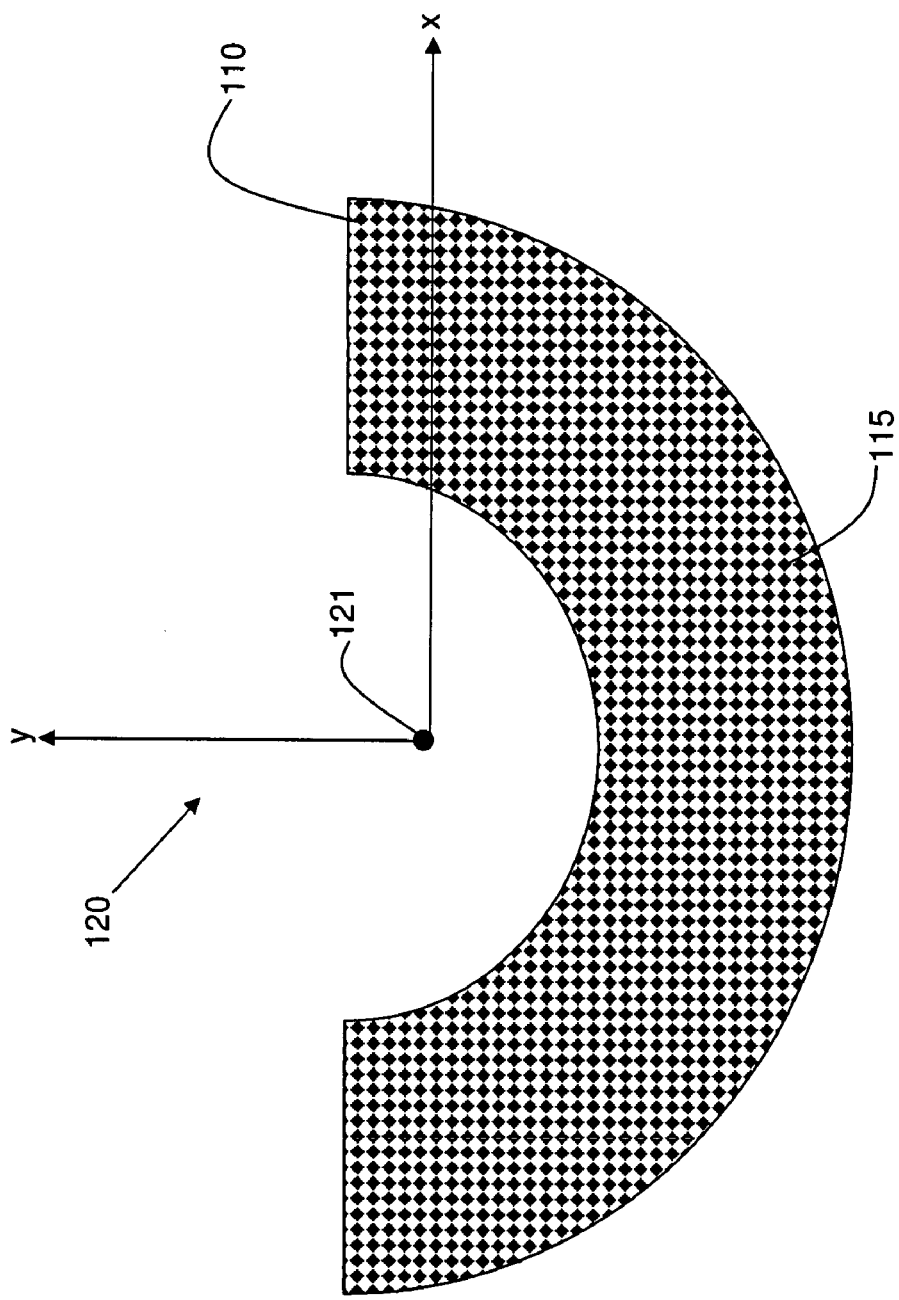
FIG. 5 illustrates an embodiment of a bite plate used in the system of FIG. 1.

FIG. 4 illustrates an example of an upper dentition 400 of a patient. There is a gap 410 in the dentition 400 due to, for example, a missing tooth. FIG. 5 illustrates an embodiment of the bite plate 110 used in the system 100 of FIG. 1. The bite plate 110 includes a plurality of pressure sensors 115 (e.g., piezoelectric sensors) covering a top surface of the bite plate 110. The bite plate 110 is shaped to fit within the mouth of a patient. Bite plates of various sizes may be provided in order to accommodate different size mouths of different patients. For example, smaller bite plates may be provided for children.

In accordance with an embodiment of the present invention, the bite plate 110 is positioned with respect to a spatial coordinate system 120 having an origin point 121. The spatial coordinate system 120 provides the spatial frame of reference that is used to ultimately position the imaging source 140 at the proper distances and angles with respect to the dentition 400. The position of each sensor 115 on the bite plate 110 is known with respect to the spatial coordinate system 120.

Figure 6:
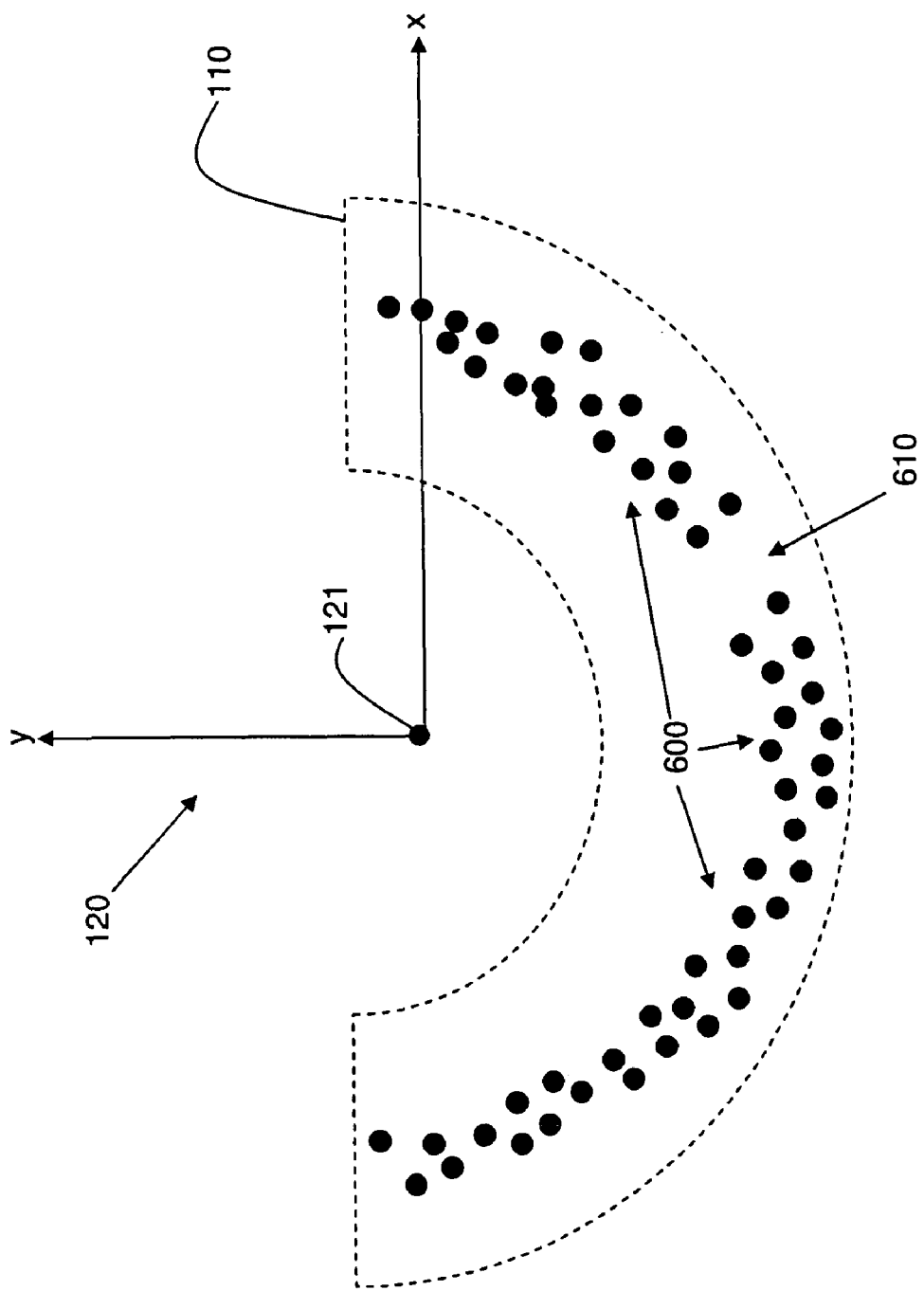
FIG. 6 illustrates a plurality of spatial pressure data points caused by the dentition of FIG. 4 and registered by the bite plate of FIG. 5.

FIG. 6 illustrates a plurality of spatial pressure data points 600 caused by the dentition 400 of FIG. 4 and registered by the bite plate 110 of FIG. 5. As the patient bites down on the bite plate 110, the piezoelectric sensors 115 will generate electrical signals at the pressure points which are captured and stored as spatial pressure data points 600. The position of each spatial pressure data point is known with respect to the spatial coordinate system 120 since the position of the bite plate 110 is known and the position of each sensor 115 on the bite plate 110 is known. Notice the gap 610 in the data points 600 corresponding to the gap 410 in the dentition.

Once the spatial pressure data points 600 are registered within the bite plate 110, the data points 600 are read by the computer-based platform 130 (via wired or wireless means). The computer-based platform 130 is capable of processing the data points 600 to form a fitted curve through the data points. In accordance with an embodiment of the present invention, the fitted curve is a best-fit curve.

Figure 7:
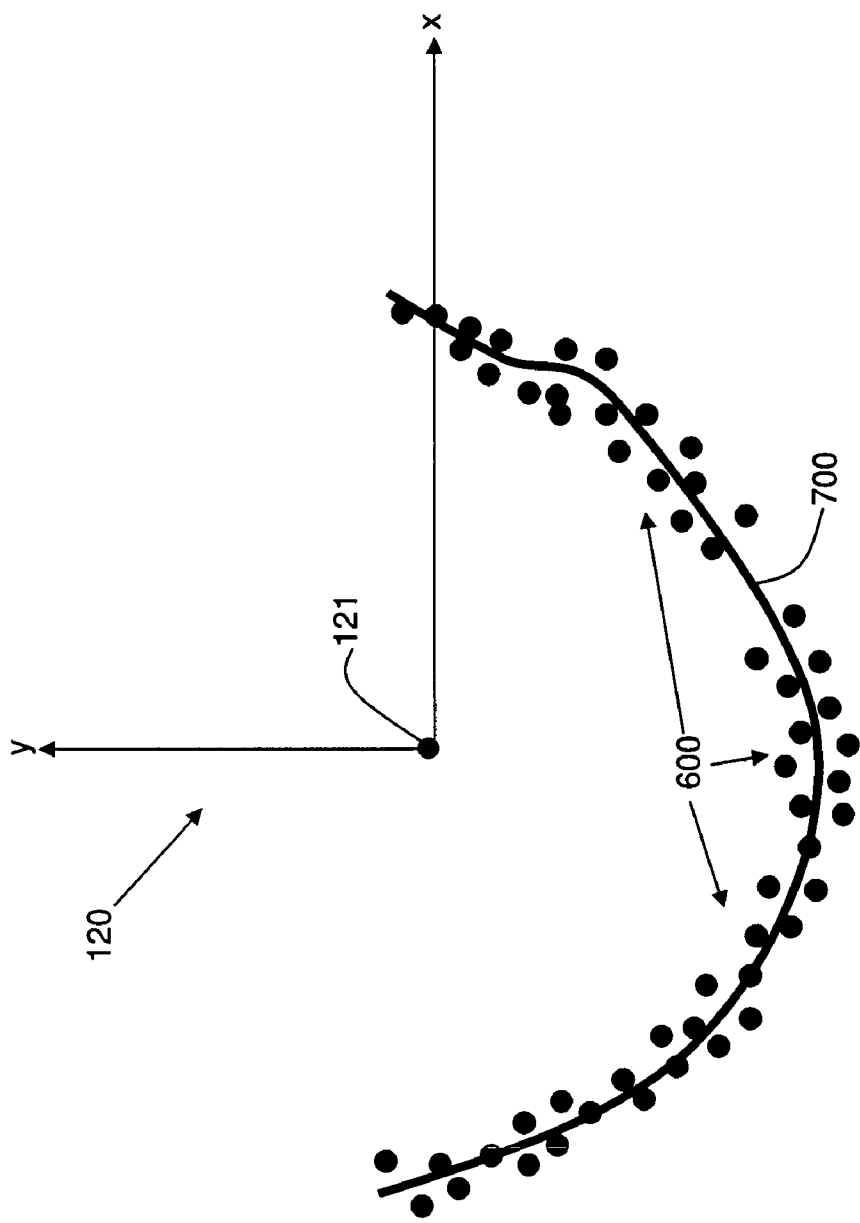
FIG. 7 illustrates a fitted curve computed by the system of FIG. 1 through the data points of FIG. 6.

FIG. 7 illustrates a fitted curve 700 computed by the system 100 of FIG. 1 through the data points 600 of FIG. 6. The fitted curve 700 essentially traces out a path through the dentition 400 in three-dimensional (or two-dimensional) space with respect to the spatial coordinate system 120. Again, the spatial coordinate system 120 is shown in two spatial dimensions (x, y) but may actually be a three-dimensional (x, y, z) coordinate system. The fitted curve 700 may be computed using a well known mathematical curve fitting technique such as, for example, a least squares technique or some other linear regression technique.

The fitted curve 700 forms the spatial basis from which an image acquisition trajectory may be computed. In the example of FIG. 7, notice that the left portion of the fitted curve 700 forms a substantially uniformly-behaved curve, whereas the right portion of the fitted curve 700 is somewhat linear over a first portion and then twists and turns over a second portion. This twisting and turning is due to mis-aligned or mis-shapen portions of the dentition 400.

Figure 8:
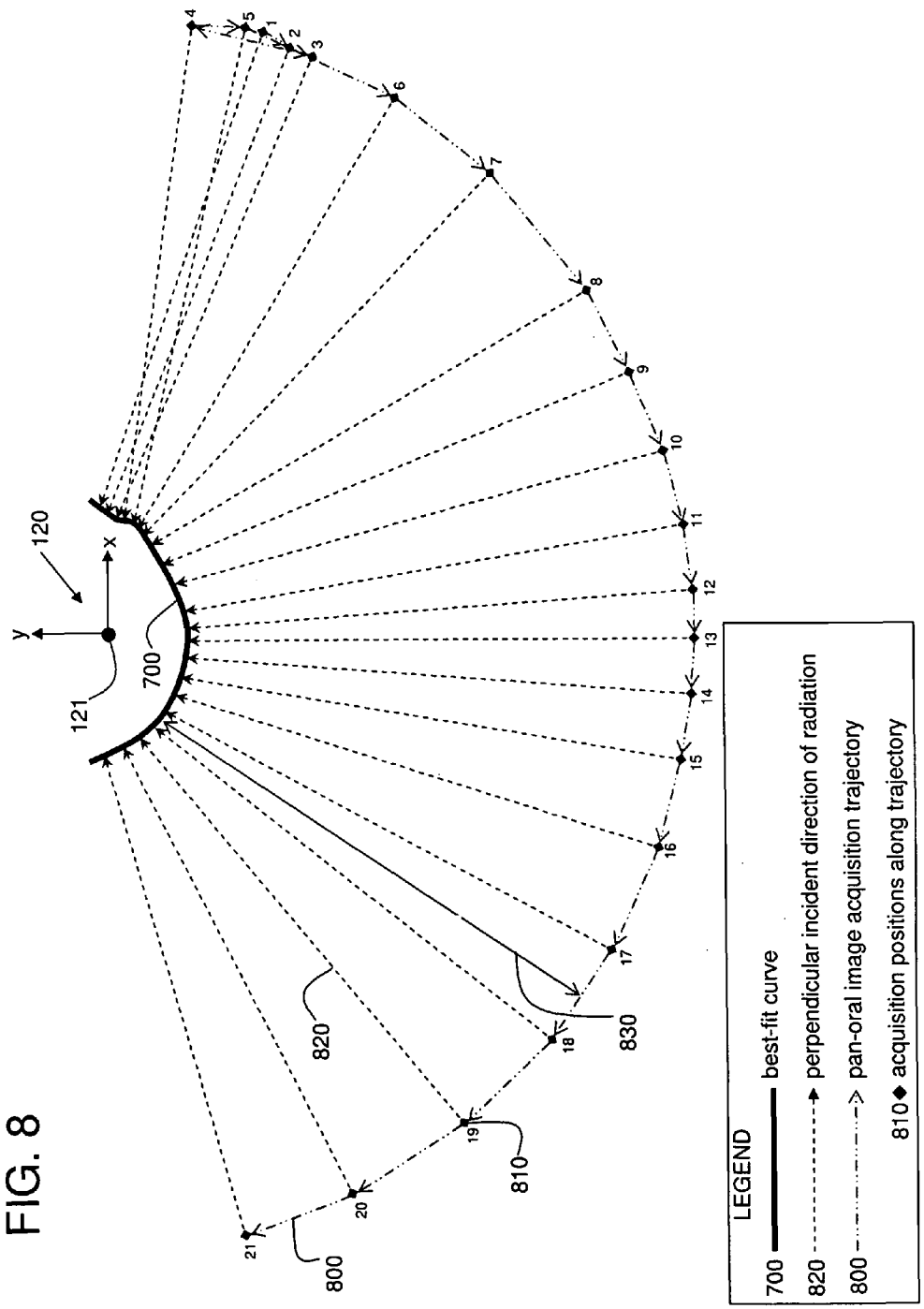
FIG. 8 illustrates a pan-oral image acquisition trajectory computed by the system of FIG. 1 using the fitted curve of FIG. 7.

FIG. 8 illustrates a pan-oral image acquisition trajectory 800 computed by the system 100 of FIG. 1 using the fitted curve 700 of FIG. 7. Once the fitted curve 700 is computed, a pan-oral image acquisition trajectory 800 may be computed based on the fitted curve 700. In accordance with an embodiment of the present invention, it is desirable to position the imaging source 140 such that an incident direction of radiation from the imaging source 140 towards a point to be imaged on the fitted curve 700 is substantially perpendicular to the fitted curve 700 at that point to be imaged, and that the point to be imaged is at a defined focal distance 830 from the imaging source 140. In general, the scanning or image acquisition direction is shown in FIG. 8 as being from right to left along the image acquisition trajectory 800 from points 1 to 21. However, as described later herein, this right to left scanning may not be strictly adhered to.

The assumption is that, using this perpendicular orientation and the focal distance, the dentition 400 at the point to be imaged on the fitted curve 700 will also be substantially perpendicular to the incident direction of radiation and at the focal distance, thus providing a clear and sharp image of the dentition. During image acquisition, the imaging subsystem is continuously re-positioned at points along the image acquisition trajectory 800 in a similar manner (i.e., perpendicular and at the focal distance) in order to acquire and construct a full pan-oral image as the imaging source 140 traverses the pan-oral image acquisition trajectory 800.

FIG. 8 shows twenty-one acquisition positions 810 (i.e., points 1-21) and twenty-one associated perpendicular incident directions of radiation 820 along the computed image acquisition trajectory 800. There may be many more intermediate acquisition points making up the image acquisition trajectory 800, however. Twenty-one points are shown for the purpose of illustrating the concept. The points along the image acquisition trajectory 800 are computed such that the incident directions of radiation 820 are substantially perpendicular to the fitted curve 700 and such that the acquisition points 810 on the image acquisition trajectory 800 are substantially at a defined focal distance 830 from the fitted curve 800. A known geometric projection technique may be used to compute the pan-oral image acquisition trajectory 800 using the fitted curve 700.

The right portion of the image acquisition trajectory 800 is associated with the right portion of the fitted curve 700. Again, the right portion of the fitted curve 700 is linear over one portion and then twists and turns over another portion due to mis-aligned or mis-shapen portions of the dentition 400. When generating points on the image acquisition trajectory 800, which are at a focal distance 830 and project substantially perpendicularly to points on the fitted curve 700, it may be seen from the right portion of FIG. 8 that certain image acquisition points (i.e., points 1-5) do not all appear in the general right to left scanning order.

In order to acquire images of dentition strictly from right to left along the fitted curve 700 in correct anatomical order, the imaging source 140 would start at acquisition point 1 and proceed to acquisition points 2, 3, 4, 5, etc. in order. However, acquisition points 1 through 5 are not in right to left order on the image acquisition trajectory 800. This is because, in order to remain substantially perpendicular to and at a defined focal distance 830 from the fitted curve 700, the imaging source 140 has to start at acquisition point 1 and then proceed to acquisition point 2 then point 3, which are to the left of acquisition point 1, and then proceed to acquisition point 4 which is to the right of acquisition point 1 along the trajectory 800. Then the imaging source 140 proceeds to acquisition point 5 which is to the left of acquisition point 4 along the trajectory 800 but is still to the right of acquisition point 1. Then the imaging source moves a significant distance to acquisition point 6 along the trajectory going to the left along the trajectory 800, and completes the acquisition going from points 6 to 21 from right to left along the trajectory 800. In this manner, imaging data is acquired along the fitted curve 700 in correct anatomical order from right to left. As a result, a focal trough formed by the imaging source 140 (e.g., an x-ray imaging source) will encapsulate or contain the fitted curve 700.

In accordance with an alternative embodiment of the present invention, the imaging data may be acquired by traversing the trajectory 800 strictly from right to left starting at point 4 and going to point 5, then going to point 1, then point 2, then point 3, then point 6, etc. However, the imaging data of the dentition 400 along the fitted curve 700 would not be acquired in correct anatomical order and would then have to be reconstructed to put in correct anatomical order. Such an alternative embodiment is quite feasible in a digital system that is capable of performing digital image reconstruction.

In accordance with an alternative embodiment of the present invention, the imaging subsystem may have its own spatial coordinate system. In such an alternative embodiment, the computed pan-oral image acquisition trajectory is transformed from the spatial coordinate system 120 to the spatial coordinate system of the imaging subsystem.

A further embodiment of the present invention comprises a computer program product, comprising a computer usable medium (e.g., a compact disk (CD) or a memory device) having a computer readable program code (i.e., a software application) embedded therein. The computer readable program code is adapted to be executed by the computer-based platform 130 to implement a method of generating a pan-oral image acquisition trajectory 800, as described herein, from a plurality of data points representing spatial locations of an actual dentition of a patient. For example, the method may include reading a plurality of data points representative of spatial locations of an actual dentition of a patient with respect to a defined spatial coordinate system, computing a fitted curve through at least a portion of the spatial positions of the dentition using the plurality of data points, and computing points of image acquisition that are projected substantially perpendicularly outward from points along the fitted curve at a defined focal distance within the defined spatial coordinate system. The points of image acquisition define a pan-oral image acquisition trajectory which may be traversed by an image acquisition source.

In summary, a system, method, and computer program product for performing pan-oral imaging is disclosed. A plurality of data points are generated which are representative of spatial positions of an actual dentition of a patient with respect to a defined spatial coordinate system. A fitted curve through at least a portion of the spatial positions of the dentition is computed using the plurality of data points. A pan-oral image acquisition trajectory is then computed with respect to a defined spatial coordinate system using the fitted curve. A pan-oral image of the dentition is then acquired along the pan-oral image acquisition trajectory.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiment disclosed, but that the claimed subject matter will include all embodiments falling within the scope of the appended claims.

What is claimed is:

1. A method of performing pan-oral imaging, said method comprising:

generating a plurality of data points representative of spatial positions of an actual dentition of a patient with respect to a defined spatial coordinate system;

computing a fitted curve through at least a portion of said spatial positions of said dentition using said plurality of data points;

computing a pan-oral image acquisition trajectory with respect to said defined spatial coordinate system using said fitted curve; and acquiring a pan-oral image of said dentition along said pan-oral image acquisition trajectory in an anatomical order providing an incident direction of x-ray radiation substantially perpendicular to points along said fitted curve by allowing at least a portion of said acquiring to take place in a spatially non-sequential scanning order along said pan-oral image acquisition trajectory.

2. The method of claim 1 wherein said fitted curve is computed from spatial positions of an upper dentition of said patient.

3. The method of claim 1 wherein said fitted curve is computed from spatial positions of a lower dentition of said patient.

4. The method of claim 1 wherein said fitted curve is computed from spatial positions of an upper and a lower dentition of said patient.

5. The method of claim 1 wherein said acquiring is accomplished, at least in part, by forming a focal trough containing said fitted curve within said defined spatial coordinate system.

6. The method of claim 1 wherein said computing of said fitted curve is accomplished using a least squares technique.

7. The method of claim 1 wherein said computing of said fitted curve is accomplished using a linear regression technique.

8. A method of performing pan-oral imaging, said method comprising:

providing a bite plate having a known spatial position and orientation in three-dimensional space with respect to a defined three-dimensional spatial coordinate system;

having a patient position said bite plate within a mouth of said patient and bite down on said bite plate;

said bite plate producing a plurality of electrical signals in response to said biting down, wherein said plurality of electrical signals are representative of spatial positions of a dentition of said patient with respect to said defined three-dimensional spatial coordinate system;

communicating said plurality of electrical signals to a computer-based platform;

said computer-based platform computing a fitted curve through at least a portion of said spatial positions of said dentition in response to said electrical signals;

said computer-based platform computing a pan-oral image acquisition trajectory with respect to said defined three-dimensional spatial coordinate system in response to said fitted curve; and acquiring a pan-oral image of said dentition in an anatomical order providing an incident direction of x-ray radiation from an x-ray source substantially perpendicular to points along said fitted curve by allowing said x-ray source to move in a spatially non-sequential scanning order along at least a portion of said pan-oral image acquisition trajectory.

9. The method of claim 8 wherein said fitted curve is computed from spatial positions of an upper dentition of said patient.

10. The method of claim 8 wherein said fitted curve is computed from spatial positions of a lower dentition of said patient.

11. The method of claim 8 wherein said fitted curve is computed from spatial positions of an upper and a lower dentition of said patient.

12. The method of claim 8 wherein said acquiring is accomplished, at least in part, by said x-ray source forming a focal trough containing said fitted curve within said defined three-dimensional spatial coordinate system.

13. The method of claim 8 wherein said computing of said fitted curve is accomplished using a least squares technique.

14. The method of claim 8 wherein said computing of said fitted curve is accomplished using a linear regression technique.

15. The method of claim 8 wherein said bite plate includes a plurality of pressure sensors each capable of converting an applied pressure to an electrical signal.

16. A system for performing pan-oral imaging, said system comprising:
   means for generating a plurality of electrical signals representative of spatial positions of an actual dentition of a patient with respect to a defined spatial coordinate system;
   means for computing a fitted curve through at least a portion of said spatial positions of said dentition using said plurality of electrical signals;
   means for computing a pan-oral image acquisition trajectory with respect to said defined spatial coordinate system using said fitted curve; and
   means for acquiring a pan-oral image of said dentition in an anatomical order along said pan-oral image acquisition trajectory, wherein said means for acquiring is configured to provide an incident direction of x-ray radiation substantially perpendicular to points along said fitted curve and allow at least a portion of said acquiring to take place in a spatially non-sequential scanning order along said pan-oral image acquisition trajectory.

17. The system of claim 16 wherein said fitted curve is computed from spatial positions of an upper dentition of said patient.

18. The system of claim 16 wherein said fitted curve is computed from spatial positions of a lower dentition of said patient.

19. The system of claim 16 wherein said fitted curve is computed from spatial positions of an upper and a lower dentition of said patient.

20. The system of claim 16 wherein said means for computing said fitted curve uses a least squares technique.

21. The system of claim 16 wherein said means for computing said fitted curve uses a data linear regression technique.

22. The system of claim 16 wherein said means for acquiring is capable of forming a focal trough containing said fitted curve within said defined spatial coordinate system.

23. A method of generating a pan-oral image acquisition trajectory for an x-ray imaging source, said method comprising:
   providing a pressure sensitive bite plate having a known spatial position and orientation in three-dimensional space with respect to a defined three-dimensional spatial coordinate system;
   having a patient position said bite plate within a mouth of said patient and bite down on said bite plate to create points of pressure on said bite plate;
   said bite plate producing a plurality of electrical signals in response to said biting down, wherein said plurality of electrical signals are representative of spatial positions of a dentition of said patient at said points of pressure with respect to said defined three-dimensional spatial coordinate system;
   communicating said plurality of electrical signals to a computer-based platform;
   said computer-based platform computing a fitted curve through at least a portion of said spatial positions of said dentition in response to said electrical signals; and
   said computer-based platform computing a pan-oral image acquisition trajectory with respect to said defined three-dimensional spatial coordinate system in response to said fitted curve, wherein said pan-oral image acquisition trajectory allows for acquisition of a pan-oral image of said dentition in an anatomical order by allowing at least a portion of said acquisition to take place in a spatially non-sequential scanning order along said pan-oral image acquisition trajectory providing an incident direction of x-ray radiation that is substantially perpendicular to points along said fitted curve.

24. The method of claim 23 wherein said fitted curve is computed from spatial positions of an upper dentition of said patient.

25. The method of claim 23 wherein said fitted curve is computed from spatial positions of a lower dentition of said patient.

26. The method of claim 23 wherein said fitted curve is computed from spatial positions of an upper and a lower dentition of said patient.

27. The method of claim 23 wherein said computing of said fitted curve is accomplished using a least squares technique.

28. The method of claim 23 wherein said computing of said fitted curve is accomplished using a linear regression technique.

29. A computer program product, comprising a computer usable medium having a computer readable program code embedded therein, said computer readable program code adapted to be executed to implement a method for generating a pan-oral image acquisition trajectory, said method comprising:
   reading a plurality of data points representative of spatial locations of an actual dentition of a patient with respect to a defined spatial coordinate system;
   computing a fitted curve through at least a portion of said spatial positions of said dentition using said plurality of data points; and
   computing points of image acquisition that are projected substantially perpendicularly outward from points along said fitted curve at a defined focal distance within said defined spatial coordinate system, wherein said points of image acquisition define a pan-oral image acquisition trajectory which may be traversed by an image acquisition source in a spatially non-sequential scanning order to acquire a pan-oral image of said dentition in an anatomical order.

30. The computer program product of claim 29 wherein said computing of said fitted curve is accomplished using a least squares technique.

31. The computer program product of claim 29 wherein said computing of said fitted curve is accomplished using a linear regression technique.

32. The computer program product of claim 29 wherein said computing of said points of image acquisition is accomplished using geometric projection techniques.

* * * * *